(12) United States Patent
Chen et al.

(10) Patent No.: US 7,371,878 B2
(45) Date of Patent: *May 13, 2008

(54) TANTALUM AMIDE COMPLEXES FOR DEPOSITING TANTALUM-CONTAINING FILMS, AND METHOD OF MAKING SAME

(75) Inventors: Tianniu Chen, Rocky Hill, CT (US); Chongying Xu, New Milford, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 104 days.

This patent is subject to a terminal disclaimer.

(21) Appl. No.: 11/625,918

(22) Filed: Jan. 23, 2007

(65) Prior Publication Data

US 2007/0117385 A1    May 24, 2007

Related U.S. Application Data

(63) Continuation of application No. 11/224,588, filed on Sep. 12, 2005, now Pat. No. 7,198,815, which is a continuation of application No. 10/684,545, filed on Oct. 14, 2003, now Pat. No. 6,960,675.

(51) Int. Cl.
*C07F 9/00* (2006.01)
*B05D 5/06* (2006.01)
(52) U.S. Cl. .......................................... 556/42; 427/69
(58) Field of Classification Search ..................... None
See application file for complete search history.

(56) References Cited

U.S. PATENT DOCUMENTS

| | | | |
|---|---|---|---|
| 5,204,314 A | 4/1993 | Kirlin et al. | |
| 5,711,816 A | 1/1998 | Kirlin et al. | |
| 5,820,664 A | 10/1998 | Gardiner et al. | |
| 6,015,917 A | 1/2000 | Bhandari et al. | |
| 6,552,209 B1 | 4/2003 | Lei et al. | |
| 6,593,484 B2 | 7/2003 | Yasuhara et al. | |
| 6,960,675 B2 * | 11/2005 | Chen et al. .................... | 556/42 |

* cited by examiner

*Primary Examiner*—Shaojia Anna Jiang
*Assistant Examiner*—M Louisa Lao
(74) *Attorney, Agent, or Firm*—Steven J. Hultquist; Intellectual Property Technology Law; Maggie Chappuis

(57) ABSTRACT

Tantalum precursors useful in depositing tantalum nitride or tantalum oxides materials on substrates, by processes such as chemical vapor deposition and atomic layer deposition. The precursors are useful in forming tantalum-based diffusion barrier layers on microelectronic device structures featuring copper metallization and/or ferroelectric thin films.

20 Claims, 4 Drawing Sheets

TANTALUM AMIDE COMPLEXES FOR DEPOSITING TANTALUM-CONTAINING FILMS, AND METHOD OF MAKING SAME

CROSS REFERENCE TO RELATED APPLICATIONS

This is a continuation of U.S. patent application Ser. No. 11/224,588 for "Tantalum Amide Complexes for Depositing Tantalum-Containing Films, and Method of Making Same" filed on Sep. 12, 2005 now U.S. Pat. No. 7,198,815 in the name of Tianniu Chen et al., which in turn is a continuation of U.S. patent application Ser. No. 10/684,545 for "Tantalum Amide Complexes for Depositing Tantalum-Containing Films, and Method of Making Same" filed on Oct. 14, 2003 in the name of Tianniu Chen et al. and issued Nov. 1, 2005 as U.S. Pat. No. 6,960,675.

BACKGROUND OF THE INVENTION

1. Field of the Invention

The present invention relates to tantalum-amido precursors useful in depositing Ta-containing material on a substrate, e.g., thin film layers of tantalum nitride or tantalum oxide, as well as to the synthesis of such precursors and to deposition methods employing same.

2. Description of the Related Art

Copper is of great interest for use in metallization of VLSI microelectronic devices because of its low resistivity and contact resistance, as well as its ability to enhance device performance (relative to aluminum metallization) by reducing RC time delays and thereby yielding faster microelectronic devices. Copper chemical vapor deposition (CVD) processes useful in large-scale manufacturing of microelectronic devices, e.g., in conformal filling of high aspect ratio inter-level vias in high density integrated circuits, are actively being developed and implemented by the electronics industry.

Although Cu CVD has enjoyed progressively wider usage in semiconductor manufacturing, various problems have resisted solution in the integration of copper in such microelectronic device applications. It is well established that copper diffuses relatively rapidly through many materials, including both metals and dielectrics, especially at temperatures above ~300° C., resulting in degradation of device performance and reliability, in some instances to the point of inoperability of the microelectronic device.

To inhibit diffusion of copper in microelectronic devices, barrier materials have been developed that separate copper metallization regions from vulnerable device regions, to ensure the long-term reliability of the copper-based metallurgy in integrated circuits (IC). Effective barrier materials generally must possess several characteristics, including a low diffusion coefficient for copper, low electrical resistivity, good thermal stability, effective adhesive interfaces, and the ability to form good nucleation surfaces to promote <111> texture in the deposited copper layer.

To achieve effective barrier performance, deposition of the barrier material desirably involves good step coverage in high-aspect-ratio device features, e.g., dual-damascene trench and via structures. With progressively increasing shrinkage of feature sizes in computer chips, CVD and atomic layer deposition (ALD) of the barrier material have proved advantageous over sputtering and physical vapor deposition (PVD) in achieving uniform-thickness conformal thin films with good step coverage in high-aspect ratio device features.

TaN and TaSiN have been demonstrated as suitable metal diffusion barrier materials. CVD of TaN is currently carried out using $Ta(NMe_2)_5$, penta(dimethylamino)tantalum (PDMAT). PDMAT is a solid source precursor that decomposes above 80° C. and has a limited volatility. As such, sublimation is necessary to deposit high purity tantalum-containing films, resulting in increased deposition system complexity and costs, relative to CVD utilizing liquid-phase source reagents.

$Ta(NEt_2)_5$, penta(diethylamino)tantalum (PDEAT) is a liquid, but it is unstable under elevated temperature conditions, readily decomposing to a tantalum imide species, $Ta(=NEt)(NEt_2)_3$, upon heating and therefore, unsatisfactory as a liquid source reagent for TaN barrier layer formation.

t-BuN=$Ta(NEt_2)_3$, tert-butylimino-tris-(diethylamino)tantalum (TBTDET) is a liquid at room temperature and has been proposed as a precursor for depositing TaN, but it has various unfavorable characteristics that limit its utility. Chief among these is the fact that deposition temperatures higher than 600° C. are needed to deposit suitably low resistivity films. Another problem with TBTDET is that too much carbon is incorporated in the deposited tantalum-containing film, and the resulting high carbon layers are highly resistive, and have low density and reduced effectiveness as diffusional barriers.

TaSiN has been proposed as a diffusion barrier material. CVD processes for the formation of this ternary barrier layer material have been the focus of associated development efforts. CVD of TaSiN has been carried out using PDMAT as the tantalum source and silane as the silicon source. $TaCl_5$ in combination with silane and ammonia also has been used for forming TaSiN films. Apart from hazards associated with handling pyrophoric gases such as silane, such approaches require dual source reactor configurations to accommodate the multiple precursor species ($TaCl_5$ or $Ta(NMe_2)_5$ as the tantalum reagent and silane as the silicon source). The use of dual source reactor configurations in turn significantly increases the cost and complexity of the semiconductor manufacturing operation, relative to the use of a single source reagent.

In all instances, the formation of a Ta-based diffusion barrier by chemical vapor deposition requires an effective CVD approach. The CVD process must achieve conformal coating of inter-level (<0.15 μm) vias and sidewall. Additionally, the CVD source reagent must be storage-stable, of appropriate volatility and vaporization characteristics, with good transport and deposition characteristics for production of high-purity, electronic quality thin films. CVD source reagents for such purpose are desirably liquid in character, to facilitate liquid delivery techniques that are consistent with effective volatilization and transport of the precursor vapor and the achievement of superior conformal films on the substrate.

Among various chemical vapor deposition techniques, atomic layer deposition (ALD) has emerged in recent years as a promising candidate for deposition of thin films in device structures with very small feature dimensions. ALD is carried out to achieve successive single-monolayer depositions, in which each separate deposition step theoretically goes to saturation at a single molecular or atomic monolayer thickness and self-terminates when the monolayer formation occurs on the surface of the substrate. Single-monolayer depositions are performed a number of times until a sufficiently thick film has been deposited on the substrate.

It would therefore be a significant advance in the art to provide tantalum precursors that are readily synthesized and suitable for use in vapor deposition processes such as ALD or other CVD techiques, that are robust, that possess good volatilization, transport and deposition characteristics, that are amenable to liquid delivery, e.g., by bubbling or direct liquid injection, and that produce tantalum-containing films such as TaN, $Ta_2O_5$, TaSiN and $BiTaO_4$, as well as other Ta-nitride and Ta-oxide films, of superior quality and performance characteristics.

SUMMARY OF THE INVENTION

The present invention relates generally to tantalum source reagents useful for forming Ta-containing material on a substrate, as well as to methods of making and using such tantalum source reagents.

In one aspect, the present invention relates to a precursor composition comprising at least one tantalum species selected from the group consisting of:

(i) tethered amine tantalum complexes of the formula ($\eta^2$-$R^3N(R^4)_nNR^5)Ta(NR^1R^2)_3$:

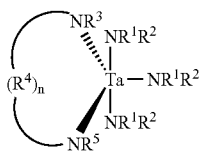

wherein:

each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

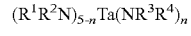

wherein m=1, 2, 3, 4, 5 or 6;

$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or $NR^8$, n must be 1; and (ii) tethered amine tantalum complexes of the formula ($\eta^2$-$R^3N(R^4)_nNR^5)_2Ta(NR^1R^2)$:

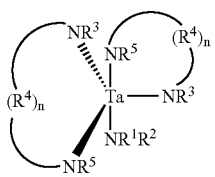

wherein:

each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

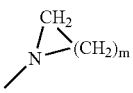

wherein m=1, 2, 3, 4, 5 or 6;

$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or $NR^8$, n must be 1; and (iii) tantalum amide compounds of the formula:

$$(R^1R^2N)_{5-n}Ta(NR^3R^4)_n$$

wherein:

each of $R^1$-$R^4$ is independently selected from the group consisting of $C_1$-$C_4$ alkyl, silyl, $C_3$-$C_8$ cycloalkyl, $C_1$-$C_4$ alkylsilyl, $C_6$-$C_{10}$ aryl, or alternatively $NR^1R^2$ or $NR^3R^4$ may be represented by the molecular moiety

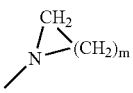

wherein m=1, 2, 3, 4, 5 or 6; and n is 1, 2, 3, or 4.

In another aspect, the invention relates to specific compounds of the foregoing formulae, specifically, $\eta^2$-N,N'-dimethylethylenediamino-tris-dimethylaminotantalum, $\eta^2$-N,N'-diethylethylenediamino-tris-dimethylaminotantalum, $\eta^2$-N,N'-dimethylpropane-diamino-tris-dimethylaminotantalum and bis-diethylamino-tris-dimethylaminotantalum.

In a further aspect, the invention relates to a method of forming Ta material on a substrate from a precursor. The method includes vaporizing the precursor to form a precursor vapor, and contacting the precursor vapor with the substrate to form the Ta material thereon, wherein the precursor includes at least one tantalum species as described hereinabove.

Yet another aspect of the invention relates to a process for making tantalum complexes of formula (I):

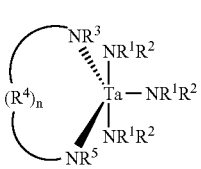

(I)

wherein:
each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

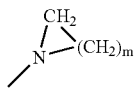

wherein m=1, 2, 3, 4, 5 or 6;
$R^4$ is selected from the group consisting of $C_1$-$C_4$ alkylene, silylene (—SiH$_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and
n is 1, 2, 3, or 4, but where $R^4$ is silylene, $C_1$-$C_4$ dialkylsilylene or $NR^8$, n must be 1;
such process including reacting a compound of formula (IV) with LiNR$^5$(R$^4$)$_n$NR$^3$Li:

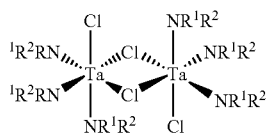 (IV)

wherein $R^1$-$R^5$ and n are as defined above.
Still another aspect of the invention relates to a process for making a tantalum complex of formula II:

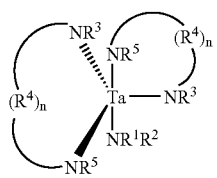 (II)

wherein:
each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

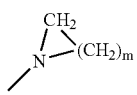

wherein m=1, 2, 3, 4, 5 or 6;
$R^4$ is selected from the group consisting of $C_1$-$C_4$ alkylene, silylene (—SiH$_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and
n is 1, 2, 3, or 4, but where $R^4$ is silylene, $C_1$-$C_4$ dialkylsilylene or $NR^8$, n must be 1; and;
such process comprising:
reacting TaX$_5$ with LiNR$^5$(R$^4$)$_n$NR$^3$Li to yield a compound of formula (V):

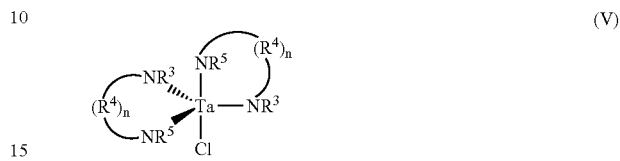 (V)

wherein $R^3$-$R^5$ and n are as defined above and X=Cl, Br or I; and
reacting the compound of formula (V) with LiN(R$^1$R$^2$), wherein $R^1$ and $R^2$ are as defined above.
In a further aspect, the invention relates to a process for making a tantalum amide compound of the formula (III):

$(R^1R^2N)_{5-n}Ta(NR^3R^4)_n$ (III)

wherein:
each of $R^1$-$R^4$ is independently selected from the group consisting of $C_1$-$C_4$ alkyl, silyl, $C_3$-$C_8$ cycloalkyl, $C_1$-$C_4$ alkylsilyl, $C_6$-$C_{10}$ aryl, or alternatively $NR^1R^2$ or $NR^3R^4$ may be represented by the molecular moiety

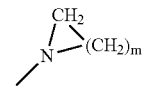

wherein m=1, 2, 3, 4, 5 or 6; and
n is 1, 2, 3, or 4.
such process comprising
reacting compound (IV) with LiNR$^3$R$^4$:

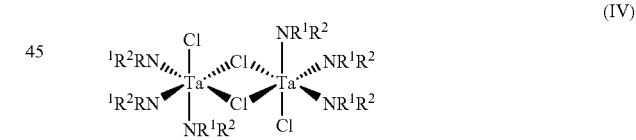 (IV)

wherein $R^1$-$R^4$ are as defined above.
Other aspects and features of the invention will be more fully apparent from the ensuing disclosure and appended claims.

DETAILED DESCRIPTION OF THE INVENTION, AND PREFERRED EMBODIMENTS THEREOF

Figure 1:
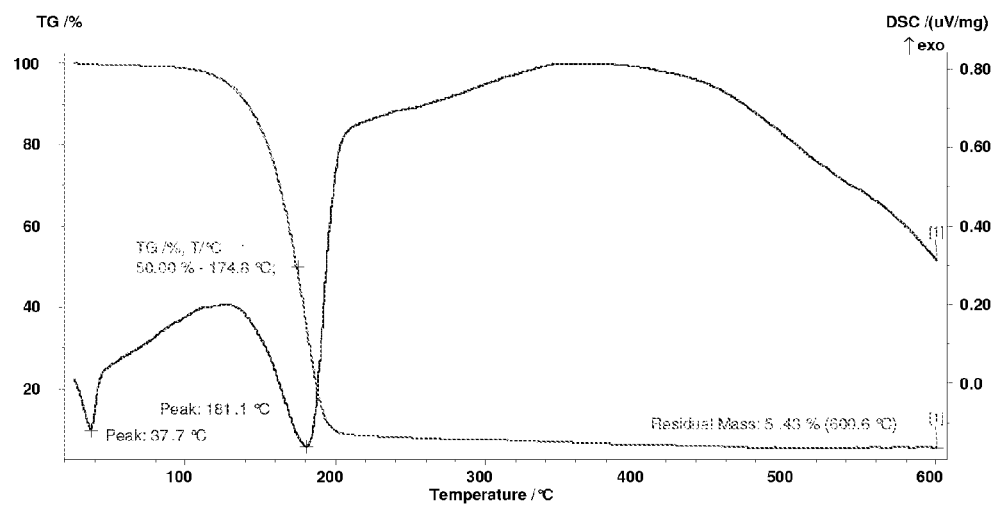
FIG. 1 is a Simultaneous Thermal Analysis (STA) plot of 5.15 mg ($\eta^2$-MeN(CH$_2$)$_2$NMe)Ta(NMe$_2$)$_3$ (DEMAT) in Ar.

The present invention is based on the discovery of tantalum source reagents useful in forming Ta-based barrier layers on substrates, e.g., TaN, Ta$_2$O$_5$, TaSiN and BiTaO$_4$ barrier layers, for manufacture of microelectronic device structures such as integrated circuitry including copper metallization and/or ferroelectric layers.

The Ta precursors of the invention include tantalum species selected from the following group:

(i) tethered amine tantalum complexes of the formula $(\eta^2\text{-}R^3N(R^4)_nNR^5)\text{Ta}(NR^1R^2)_3$:

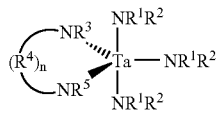

wherein:

each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as NR$^6$R$^7$, wherein $R^6$ and $R^7$ are the same as or different from one another and each is independently selected from the group consisting of H, $C_1$-$C_4$ alkyl, and $C_3$-$C_8$ cycloalkyl, or alternatively NR$^1$R$^2$ may be represented by the molecular moiety

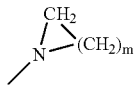

wherein m=1, 2, 3, 4, 5 or 6;

$R^4$ is selected from the group consisting of $C_1$-$C_4$ alkylene, silylene (—SiH$_2$—), $C_1$-$C_4$ dialkylsilylene and NR$^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or NR$^8$, n must be 1;

(ii) tethered amine tantalum complexes of the formula $(\eta^2\text{-}R^3N(R^4)_nNR^5)_2\text{Ta}(NR^1R^2)$:

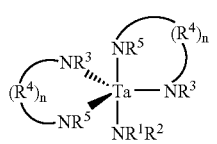

wherein:

each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as NR$^6$R$^7$, wherein $R^6$ and $R^7$ are the same as or different from one another and each is independently selected from the group consisting of H, $C_1$-$C_4$ alkyl, and $C_3$-$C_8$ cycloalkyl, or alternatively NR$^1$R$^2$ may be represented by the molecular moiety

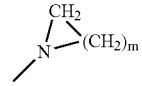

wherein m=1, 2, 3, 4, 5 or 6;

$R^4$ is selected from the group consisting of $C_1$-$C_4$ alkylene, silylene (—SiH$_2$—), $C_1$-$C_4$ dialkylsilylene and NR$^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or NR$^8$, n must be 1; and (iii) tantalum amide compounds of the formula:

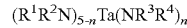

wherein:

each of $R^1$-$R^4$ is independently selected from the group consisting of $C_1$-$C_4$ alkyl, silyl, $C_3$-$C_8$ cycloalkyl, $C_1$-$C_4$ alkylsilyl, $C_6$-$C_{10}$ aryl, or alternatively NR$^1$R$^2$ or NR$^3$R$^4$ may be represented by the molecular moiety

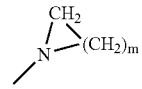

wherein m=1, 2, 3, 4, 5 or 6; and n is 1, 2, 3, or 4.

The tantalum precursors of the invention achieve a substantial advance in the art over the use of tantalum precursors previously employed for forming barrier layer films. Considering tantalum nitride as an example, the growth of tantalum nitride barrier layers desirably is carried out with precursors that are free of oxygen, so that the formation of tantalum oxide is avoided. Tantalum amides, which have preexisting Ta—N bonds, are therefore desirable in principle, but homoleptic tantalum amides such as Ta(NMe$_2$)$_5$ suffer from reduced volatility, as a result of the bridging of multiple metal centers through —NMe$_2$ groups (analogous to that observed for Ta(OEt)$_5$) and steric congestion around the Ta metal center.

By contrast, the tantalum precursors of the present invention have enhanced thermal stability and volatility as a result of their structures, which limit the degree of intermolecular interactions. For example, as compared to PDMAT with its two —NMe$_2$ groups, the use of tethered amine ligands $(\eta^2\text{-}R^3N(R^4)_nNR^5)$ in compounds of formula I below provides such monomeric tantalum amide compounds with a stable metallocyclic structure. Various tethered ligands can be employed. Ligand species of the formula $\eta^2\text{-}R^3N(R^4)_nNR^5$ wherein $R^3$ and $R^5$ are the same as or different from one another, and each is independently chosen from H, $C_1$-$C_4$ alkyl (e.g., Me, Et, t-Bu, i-Pr, etc.), aryl (e.g., phenyl, phenyl substituted with $C_1$-$C_4$ alkyl, halo, silyl or $C_1$-$C_4$ alkylsilyl, etc.), $C_3$-$C_8$ cycloalkyl, or a silicon-containing group such as silyl (SiH$_3$), $C_1$-$C_4$ alkylsilyl, (e.g., SiMe$_3$, Si(Et)$_3$, Si(i-Pr)$_3$, Si(t-Bu)$_3$) and alkyl(alkylsilyl)silyl (e.g., Si(SiMe$_3$)$_x$(Me)$_{3-x}$), $R_4$ can be $C_1$-$C_4$ alkylene (e.g. methylene, ethylene, etc.), silylene (e.g. —SiH$_2$—), $C_1$-$C_4$ dialkylsilyl (e.g. Si(CH$_3$)$_2$, etc.) or alkylamine (e.g. NCH$_3$, etc.), appropriately selected to confer a specific volatility, are preferred, wherein n is 1, 2, 3, or 4 to provide stable chelating ring structures.

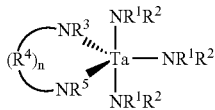

(I)

The tantalum amide compounds of formula II below feature two of the chelating $(\eta^2\text{-}R^3N(R^4)_nNR^5)$ ligands, wherein n and the various R groups are as defined in connection with formula I hereinabove.

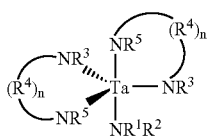

(II)

Another class of tantalum compounds of the invention include tantalum amides that are unsymmetrical in character, and utilize $(R^1R^2N)_{5-n}$ and $(NR^3R^4)_n$ as ligands of mixed ligand complexes of formula III:

$$(R^1R^2N)_{5-n}Ta(NR^3R^4)_n,$$

in which each of $R^1\text{-}R^4$ is independently chosen from $C_1\text{-}C_4$ alkyl (e.g., Me, Et, t-Bu, i-Pr, etc.), $C_6\text{-}C_{10}$ aryl (e.g., phenyl, phenyl substituted with $C_1\text{-}C_4$ alkyl, halo, silyl or $C_1\text{-}C_4$ alkylsilyl, etc.), $C_3\text{-}C_8$ cycloalkyl or a silicon-containing group such as silyl ($SiH_3$), $C_1\text{-}C_4$ alkylsilyl, (for example, $SiMe_3$, $Si(Et)_3$, $Si(i\text{-}Pr)_3$, $Si(t\text{-}Bu)_3$) and alkyl(alkylsilyl) silyl (e.g., $Si(SiMe_3)_x(Me)_{3-x}$), and n is 1, 2, 3, or 4. Alternatively, $NR^1R^2$ or $NR^3R^4$ may be represented by the molecular moiety

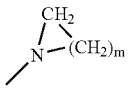

wherein m=1, 2, 3, 4, 5 or 6.

The Ta source reagents of the invention have suitable volatility characteristics for applications such as CVD.

In application to vapor deposition processes such as liquid delivery, atomic layer deposition or other chemical vapor deposition techniques, the precursors of the invention may be employed in neat liquid form, or alternatively such precursors may be utilized in formulations, e.g., in a solution or suspension of the precursor in a compatible liquid solvent or suspending medium, such as the solvent compositions disclosed in U.S. Pat. No. 5,820,664, issued Oct. 13, 1998, in the names of Robin A. Gardiner et al.

The term "liquid delivery" refers to the liquid form of the precursor composition being employed for delivery of the material to be deposited on the substrate in the vapor deposition process. When the precursor compound is a liquid phase neat material, it is vaporized to produce a corresponding precursor vapor that is then is transported to the deposition chamber, to form a film or coating of the deposition species on the substrate. Alternatively, the source reagent may be dissolved or suspended in a liquid that is vaporized to place the source reagent in the vapor phase for the deposition operation.

The solvent for such purpose can be any suitable solvent medium, e.g., a single-component solvent, or a solvent mixture of multiple solvent species. The solvent in one embodiment of the invention is selected from among $C_6\text{-}C_{10}$ alkanes, $C_6\text{-}C_{10}$ aromatics, and compatible mixtures thereof. Illustrative alkane species include hexane, heptane, octane, nonane and decane. Preferred alkane solvent species include $C_8$ and $C_{10}$ alkanes. Preferred aromatic solvent species include toluene and xylene.

It will be appreciated that various syntheses are useful for preparation of tantalum source compounds of the present invention, as will be readily apparent to those of ordinary skill in the art. Illustrative synthetic methods for production of compounds within the broad scope of the present invention are set out below by way of example, it being understood that compounds of the invention are amenable to manufacture by various other synthesis routes and methods within the skill in the art, and that the illustrative synthesis methods set out below are therefore not to be limitingly construed as regards the scope of the invention.

Synthesis Reaction Schemes for Compounds of Formula I

One illustrative synthesis scheme for compounds of formula I hereof is set out below:

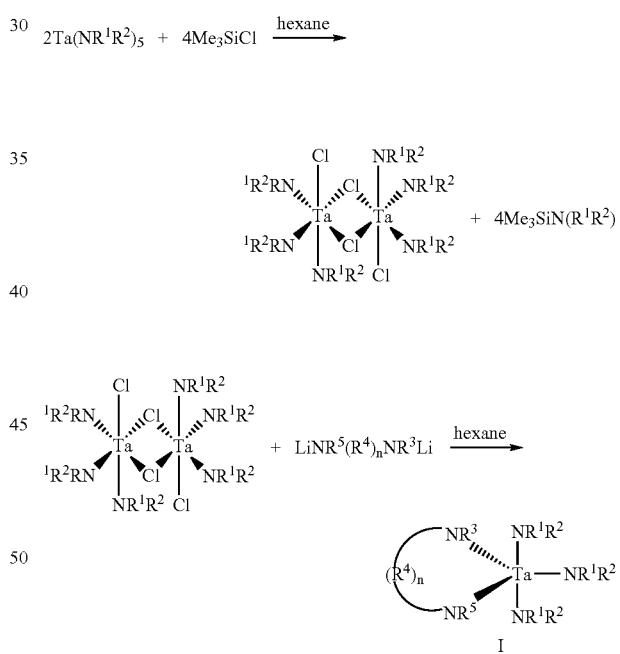

Alternatively, compounds of formula I may be synthesized as follows:

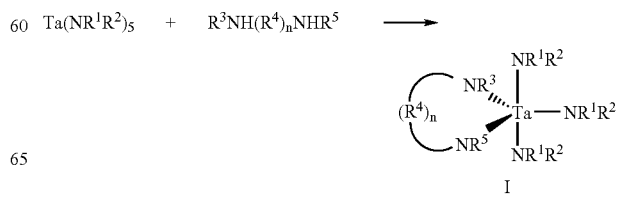

Synthesis Reaction Schemes for Compounds of Formula II

One illustrative synthesis scheme for compounds of formula II hereof is set out below:

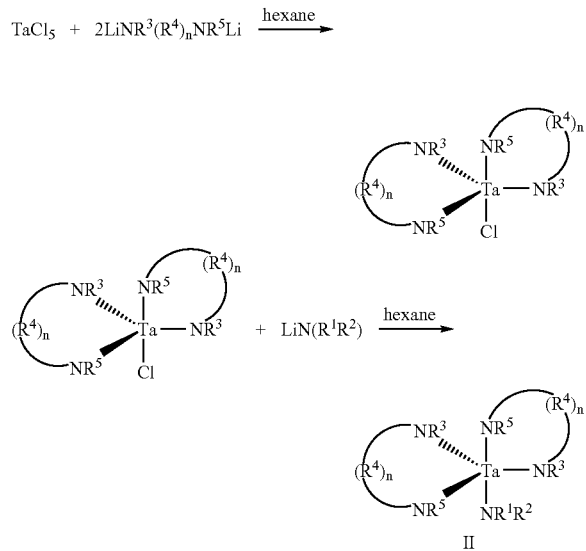

Alternatively, compounds of formula II may be synthesized as follows:

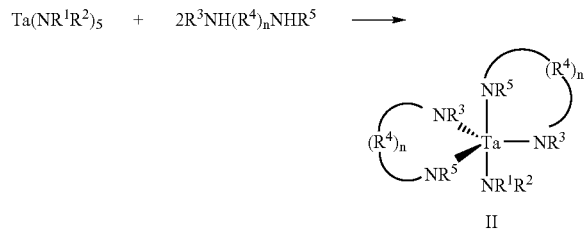

Synthesis Reaction Schemes for Compounds of Formula III

An illustrative synthesis scheme for compounds of formula III hereof is set out below:

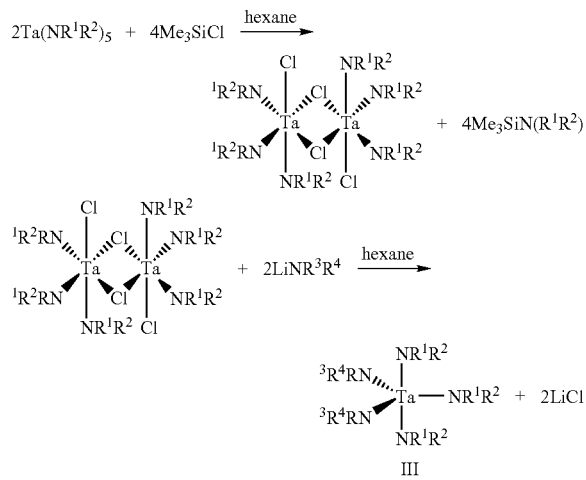

The present invention also contemplates the use of silyl amides with as single source precursors useful in forming TaSiN layers on substrates in a direct and cost-effective manner. Examples include precursors of the general formula III:

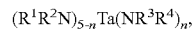

$(R^1R^2N)_{5-n}Ta(NR^3R^4)_n$, in which each of $R^1$-$R^4$ is independently chosen from $C_1$-$C_4$ alkyl (e.g., Me, Et, t-Bu, i-Pr, etc.), $C_6$-$C_{10}$ aryl (e.g., phenyl, phenyl substituted with $C_1$-$C_4$ alkyl, halo, silyl or $C_1$-$C_4$ alkylsilyl, etc.), or a silicon-containing group such as silyl ($SiH_3$), $C_1$-$C_4$ alkylsilyl, (for example, $SiMe_3$, $Si(Et)_3$, $Si(i-Pr)_3$, $Si(t-Bu)_3$) and alkyl(alkylsilyl)silyl (e.g., $Si(SiMe_3)_x(Me)_{3-x}$), and n is 1, 2, 3, or 4, with the proviso that at least one of $R^1$, $R^2$, $R^3$ and $R^4$ is a silicon-containing group. The number of silicon-containing R groups can be varied as necessary or desirable to control the amount of silicon in the film.

For liquid delivery deposition of Ta-based films or coatings on a substrate, the source reagent material is provided as a liquid starting material, e.g., as a neat liquid-phase compound, or in a suitable formulation including a solvent medium suitable for dissolving or suspending the precursor compound, and the liquid starting material then is vaporized to form the precursor vapor for the vapor deposition process.

The vaporization may be carried out by injection of the liquid, e.g., in fine jet, mist or droplet form, into a hot zone at an appropriate temperature for vaporization of the source reagent liquid. Such injection may be carried out with a nebulization or atomization apparatus of conventional character, producing a dispersion of finely-divided liquid particles, e.g., of sub-micron to millimeter diameter. The dispersed liquid particles may be directed at a substrate at a sufficiently high temperature to decompose the source reagent and produce a coating of the desired Ta-based material on the substrate.

Alternatively, the liquid may be dispensed from a suitable supply vessel containing same, so that it issues onto a volatilization element, such as a screen, grid or other porous or foraminous structure, which is heated to a sufficiently high temperature to cause the liquid to flash volatilize into the vapor phase, as described in U.S. Pat. No. 5,204,314 to Peter S. Kirlin, et al. and U.S. Pat. No. 5,711,816 to Peter S. Kirlin, et al.

Regardless of the manner of volatilization of the source reagent, the vapor thereof is flowed to contact the substrate on which the Ta-based material is to be deposited, at appropriate deposition conditions therefor, as are readily determinable within the skill of the art without undue experimentation, by the expedient of varying the process conditions (temperature, pressure, flow rate, etc.) and assessing the character and suitability of the resulting deposited material.

The deposition of the Ta material on the substrate may be carried out in the broad practice of the invention in any suitable manner, as regards the precursor compound of the invention, and the substrate and process conditions employed. For example, carrier gases may be employed for transport of the precursor vapor, such as inert gases (e.g., helium, argon, etc.) or a carrier gas appropriate to provide a desired ambient in the deposition chamber (e.g., an oxygen-containing gas, nitrogen, or other suitable carrier gas species).

In one embodiment of the invention, atomic layer deposition (ALD) is employed for depositing the Ta-based material on the substrate. For example, the ALD process may be carried out in which the substrate is exposed sequentially and alternately to at least two mutually reactive reactants. In such approach, the substrate is exposed to the first species and the first species is deposited onto the surface of the substrate until the surface is occupied with a monolayer of the first species (saturation). Following surface saturation, the supply of the first deposited species is cut-off and the reaction chamber is evacuated and/or purged to remove the traces of the first species from the gas phase. Next, the substrate is exposed to the second species which interacts with the deposited first species until the monolayer of the first species has fully interacted with the second species and the surface of the substrate is covered with a monolayer of the product of the first and second species (saturation). Following saturation by the second species, the supply of the second species is cut-off and the reaction chamber is evacuated and/or purged to remove the traces of non-reacted second species from the gas phase. This cycle can be repeated a number of times until a sufficiently thick film has been deposited onto the substrate. Notably, more than two species may be used, e.g., for the deposition of ternary or more complicated compounds or multilayers.

The features and advantages of the invention are more fully shown by the following non-limiting examples.

EXAMPLE 1

In this example, $\eta^2$-N,N'-dimethylethylenediamino-tris-dimethylaminotantalum, $(\eta^2$-MeN$(CH_2)_2$NMe)Ta$(NMe_2)_3$ (DEMAT), was synthesized at high purity and in good yield.

The synthesis of DEMAT was carried out using standard Schlenk techniques. 15.8 mL n-butyl lithium (1.6 M in hexanes, 0.025 mol) was added to a 100 mL Schlenk flask immersed in an ice bath and charged with 1.11 g N,N'-dimethylethylenediamine (0.013 mol) in 50 mL hexanes. White precipitation appeared after the addition started and the reaction was exothermic. The reaction mixture comprising MeNLi$(CH_2)_2$LiNMe was allowed to warm to room temperature. Next the MeNLi$(CH_2)_2$LiNMe mixture was added dropwise to 4.39 g [(MeN)$_3$TaCl$_2$]$_2$ (5.71 mmol) in 100 mL hexanes at room temperature and stirred overnight. Following filtration, the dark brown filtrate was recovered. The volatiles from the filtrate were removed in vacuo at room temperature followed by vacuum distillation at 79° C. and 50 mTorr to yield 3.06 g of red orange ($\eta^2$-MeN$(CH_2)_2$NMe)Ta$(NMe_2)_3$ (DEMAT) (59% yield). Atomic percentage calculated for TaC$_{10}$H$_{28}$N$_5$: C, 30.08%; H, 7.07%; N, 17.54%. Found: C, 29.89%; H, 6.94%; N, 17.52%.

FIG. 1 shows that DEMAT is thermally-stable up to its boiling temperature and undergoes complete material transport below 200° C. Further, DEMAT is volatile enough and thermally stable enough to be purified by vacuum distillation. In contrast, PDEAT and pentaethylmethylaminotantalum (PEMAT) are unstable and cannot be purified by vacuum distillation. As such, DEMAT exhibits advantages over PDMAT, PEMAT, and PDEAT in terms of thermal stability and volatility.

Figure 2:
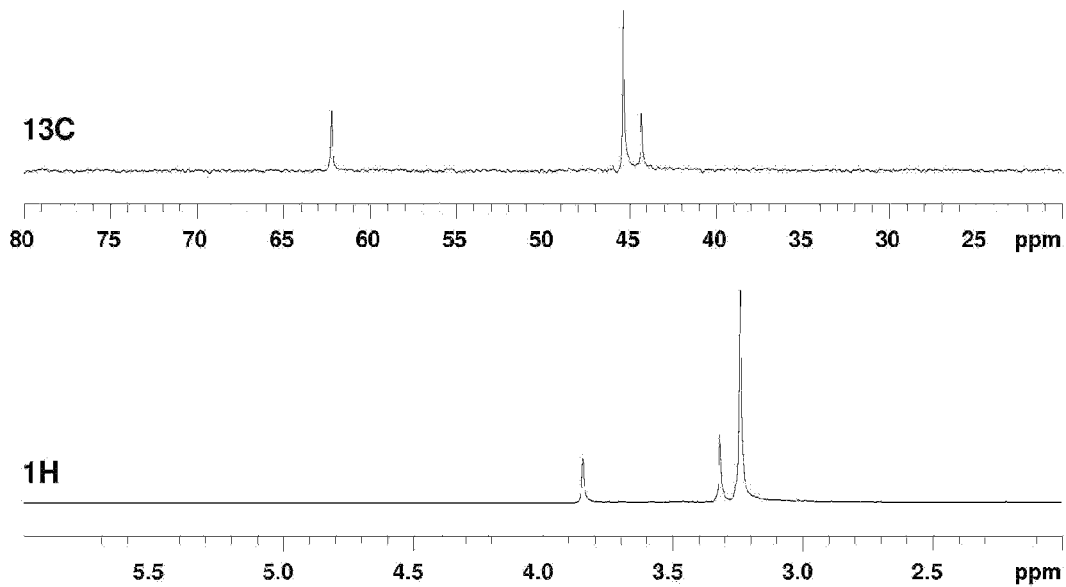
FIG. 2 is a $^1$H and $^{13}$C NMR plot for ($\eta^2$-MeN(CH$_2$)$_2$NMe)Ta(NMe$_2$)$_3$ (DEMAT) in benzene-d$_6$.

FIG. 2 shows the $^1$H and $^{13}$C NMR plot of DEMAT in benzene-d$_6$ at 21° C. $^1$H NMR: δ 3.85 (s, 4H, CH$_3$N$(CH_2)_2$—); 3.33 (s, 6H, CH$_3$N—); 3.24 (s, 18H, (CH$_3$)$_2$N—). $^{13}$C NMR plot: δ 62.20 (CH$_3$N$(CH_2)_2$—); 45.36 ((CH$_3$)$_2$N—); 44.33 (CH$_3$N$(CH_2)_2$—).

EXAMPLE 2

In this example, $\eta^2$-N,N'-diethylethylenediamino-tris-dimethylaminotantalum, $(\eta^2$-EtN$(CH_2)_2$NEt)Ta$(NMe_2)_3$ (DEMAT), was synthesized at high purity and in good yield.

The synthesis of $(\eta^2$-EtN$(CH_2)_2$NEt)Ta$(NMe_2)_3$ was carried out using standard Schlenk techniques. 13.4 mL n-butyl lithium (1.6 M in hexanes, 0.021 mol) was added to a 250 mL Schlenk flask immersed in an ice bath and charged with 1.11 g N,N'-diethylethylenediamine (0.011 mol) in 100 mL hexanes. White precipitation appeared after the addition started and the reaction was exothermic. The reaction mixture comprising EtNLi$(CH_2)_2$LiNEt was allowed to warm to room temperature. Next the EtNLi$(CH_2)_2$LiNEt mixture was added dropwise to 4.14 g [(MeN)$_3$TaCl$_2$]$_2$ (5.39 mmol) in 100 mL hexanes at room temperature and stirred overnight. Following filtration, the dark brown filtrate was recovered. The volatiles from the filtrate were removed in vacuo at room temperature followed by vacuum distillation at 77° C. and 65 mTorr to yield 2.01 g of golden yellow liquid ($\eta^2$-EtN$(CH_2)_2$NEt)Ta$(NMe_2)_3$ (44% yield). Atomic percentage calculated for TaC$_{12}$H$_{32}$N$_5$: C, 33.72%; H, 7.55%; N, 16.39%. Found: C, 33.42%; H, 7.46%; N, 16.22%.

Figure 3:
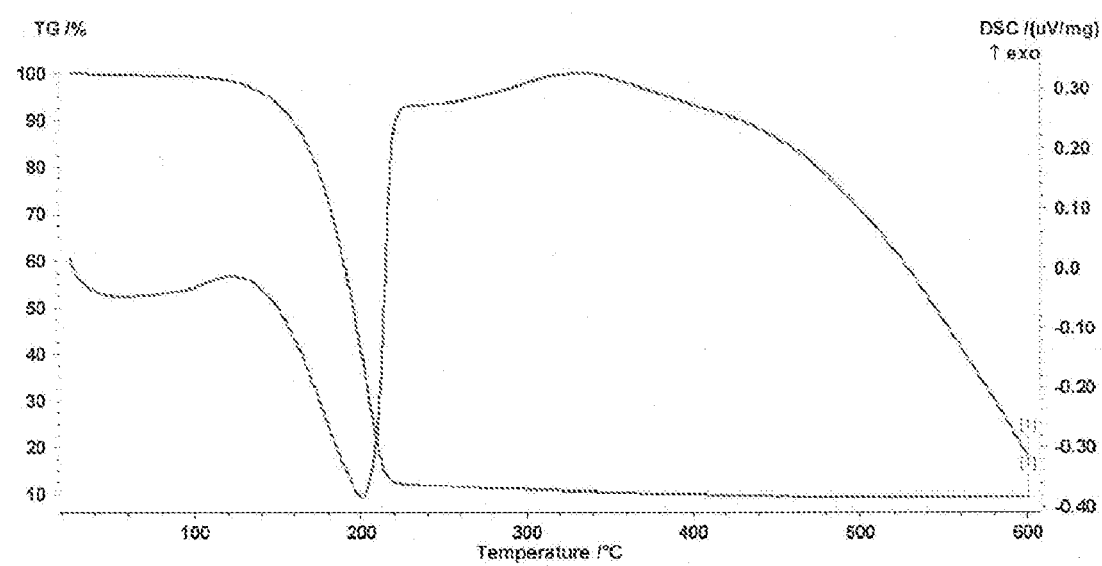
FIG. 3 is an STA plot of 9.530 mg ($\eta^2$-EtN(CH$_2$)$_2$NEt)Ta(NMe$_2$)$_3$.

FIG. 3 shows that ($\eta^2$-EtN$(CH_2)_2$NEt)Ta$(NMe_2)_3$ is thermally-stable up to its boiling temperature and undergoes complete material transport below 200° C. Further, ($\eta^2$-EtN$(CH_2)_2$NEt)Ta$(NMe_2)_3$ is a liquid and thus is volatile enough and thermally stable enough to be purified by vacuum distillation. As such, ($\eta^2$-EtN$(CH_2)_2$NEt)Ta$(NMe_2)_3$ exhibits advantages over PDMAT, PEMAT, and PDEAT in terms of thermal stability and volatility.

Figure 4:
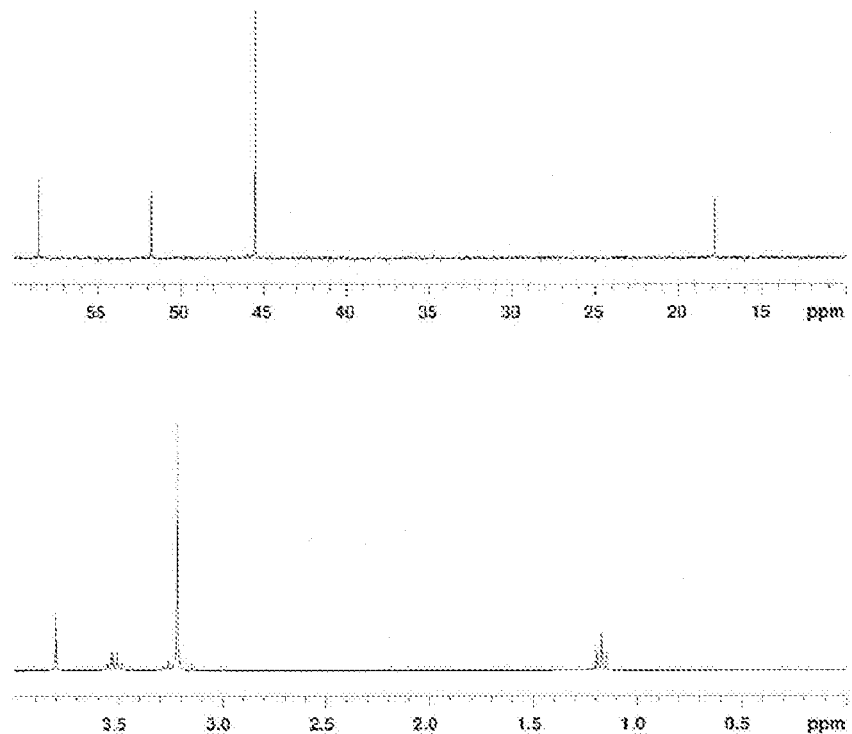
FIG. 4 is a $^1$H NMR plot for ($\eta^2$-EtN(CH$_2$)$_2$NEt)Ta(NMe$_2$)$_3$ in benzene-d$_6$.

FIG. 4 shows the $^1$H and $^{13}$C NMR plot of ($\eta^2$-EtN$(CH_2)_2$NEt)Ta$(NMe_2)_3$ in benzene-d$_6$ at 21° C. $^1$H NMR: δ 3.80 (s, 4H, CH$_3$CH$_2$N$(CH_2)_2$—); 3.52 (q, 4H, CH$_3$CH$_2$N—); 3.22 (s, 18H, (CH$_3$)$_2$N—); 1.17 (t, 6H, CH$_3$CH$_2$N—). $^{13}$C NMR plot: δ 58.54 (CH$_3$CH$_2$N$(CH_2)_2$—); 51.76 ((CH$_3$CH$_2$N$(CH_2)_2$—); 45.41 ((CH$_3$)$_2$N—); 17.80 (CH$_3$CH$_2$N$(CH_2)_2$—).

EXAMPLE 3

In this example, $\eta^2$-N,N'-dimethylpropanediamino-tris-dimethylaminotantalum, $(\eta^2$-MeN$(CH_2)_3$NMe)Ta$(NMe_2)_3$, was synthesized at high purity and in good yield.

The synthesis of ($\eta^2$-MeN$(CH_2)_3$NMe)Ta$(NMe_2)_3$ was carried out using standard Schlenk techniques. 16.4 mL n-butyl lithium (1.6 M in hexanes, 0.026 mol) was added to a 100 mL Schlenk flask immersed in an ice bath and charged with 1.34 g N,N'-dimethylpropanediamine (0.013 mol) in 50 mL hexanes. White precipitation appeared after the addition started and the reaction was exothermic. The reaction mixture comprising MeNLi$(CH_2)_3$LiNMe was allowed to warm to room temperature. Next the MeNLi$(CH_2)_3$LiNMe mixture was added dropwise to 5.02 g [(MeN)$_3$TaCl$_2$]$_2$ (6.54 mmol) in 30 mL hexanes at room temperature and stirred and refluxed at 80° C. overnight. Following filtration, the dark brown filtrate was recovered. The volatiles from the filtrate were removed in vacuo at room temperature followed by vacuum distillation at 85° C. and 50 mTorr to yield 2.05 g of yellow orange liquid ($\eta^2$-MeN$(CH_2)_3$NMe)Ta$(NMe_2)_3$ (38% yield). Atomic percentage calculated for TaC$_{11}$H$_{30}$N$_5$: C, 31.96%; H, 7.32%; N, 16.94%. Found: C, 31.74%; H, 7.46%; N, 16.82%.

Figure 5:
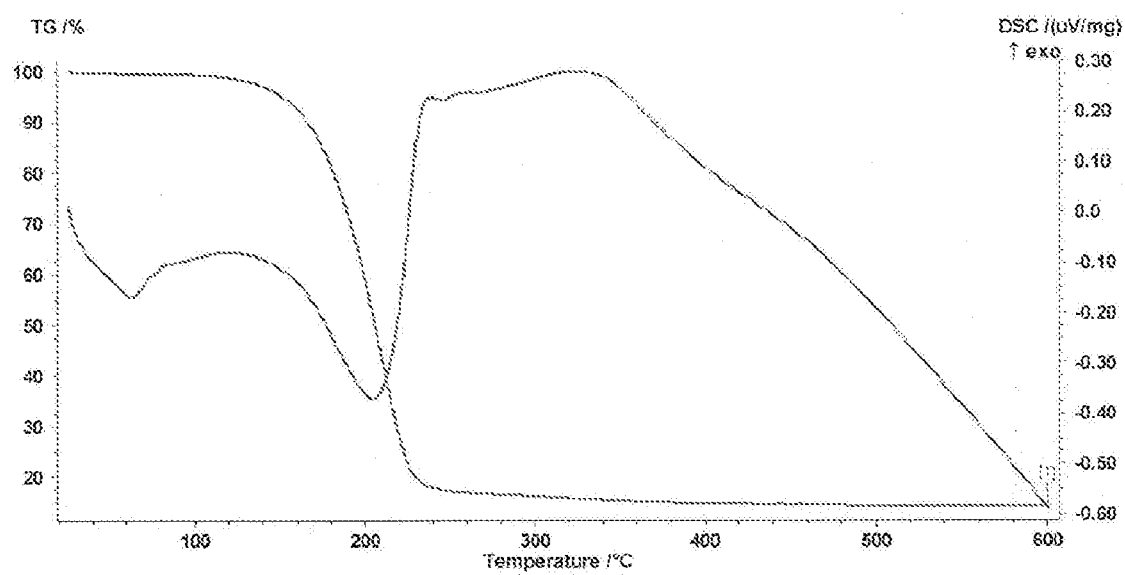
FIG. 5 is an STA plot of 12.141 mg ($\eta^2$-MeN(CH$_2$)$_3$NMe)Ta(NMe$_2$)$_3$.

FIG. 5 shows that ($\eta^2$-MeN$(CH_2)_3$NMe)Ta$(NMe_2)_3$ is thermally-stable up to its boiling temperature and undergoes complete material transport below 210° C. Further, ($\eta^2$-MeN$(CH_2)_3$NMe)Ta$(NMe_2)_3$ is volatile enough and thermally stable enough to be purified by vacuum distillation. As such, (η²-MeN(CH₂)₃NMe)Ta(NMe₂)₃ exhibits advantages over PDMAT, PEMAT, and PDEAT in terms of thermal stability and volatility.

Figure 6:
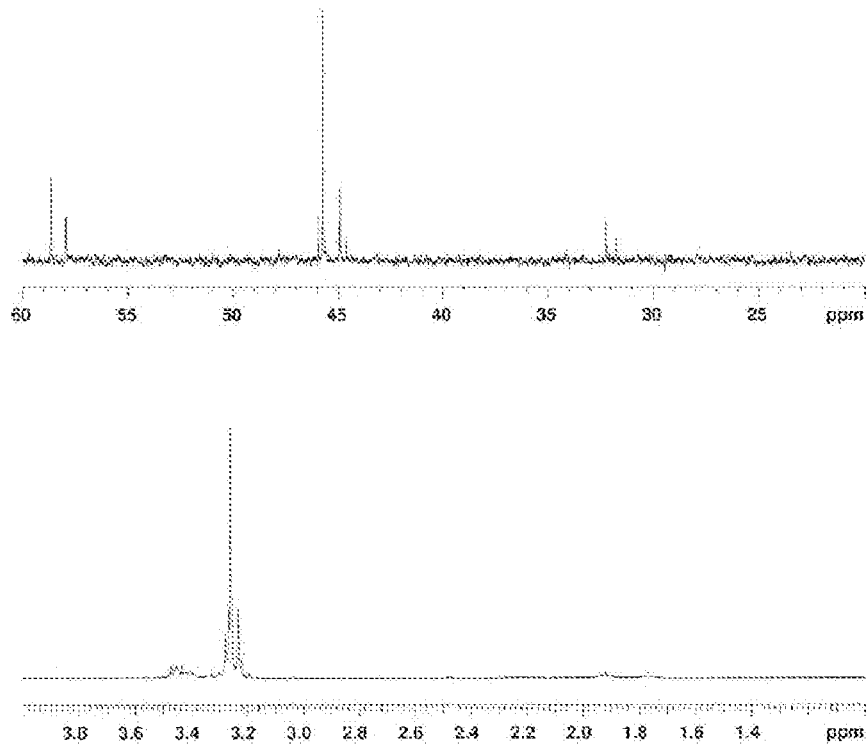
FIG. 6 is a $^1$H NMR plot for $(\eta^2\text{-MeN(CH}_2)_3\text{NMe})\text{Ta}$(NMe$_2$)$_3$ in benzene-d$_6$.

FIG. 6 shows the ¹H and ¹³C NMR plot of (η²-MeN (CH₂)₃ NMe)Ta(NMe₂)₃ in benzene-d₆ at 21° C. ¹H NMR: δ 3.44 (m, br, 4H, CH₃NCH₂—); 3.26 (s, 18H, (CH₃)₂N—); 3.22 (s, 6H, CH₃NCH₂—); 1.85 (m, 2H, CH₃NCH₂CH₂—). ¹³C NMR plot: δ 58.60, 57.88 (CH₃NCH₂—); 45.88, 45.66 ((CH₃)₂N—); 44.90, 44.61 (CH₃NCH₂—); 32.23, 31.74 (CH₃NCH₂CH₂—). The NMR spectra are consistent with the assigned structure. The complicated patterns in the ¹H spectra are attributable to cis- (when the —NMe(CH₂)₃ MeN— ligand occupies the equatorial positions in the trigonal bipyramidal geometry) and trans- isomers (when the —NMe(CH₂)₃MeN— ligand occupies the axial positions in the trigonal bipyramidal geometry) in the solution:

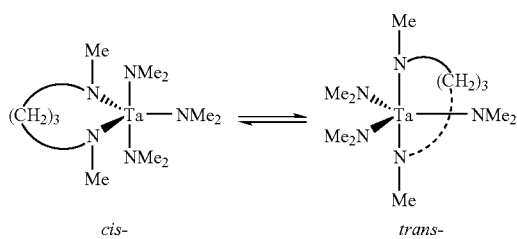

cis-    trans-

EXAMPLE 4

In this example, bis-diethylamino-tris-dimethylaminotantalum, (NEt₂)₂Ta(NMe₂)₃ was synthesized in high purity and in good yield. The synthesis of (NEt₂)₂Ta(NMe₂)₃ was carried out using standard Schlenk techniques. 32.2 mL n-butyl lithium (1.6 M in hexanes, 0.052 mol) was added to a 250 mL Schlenk flask immersed in an ice water bath and charged with 5.34 mL diethylamine (3.78 g, 0.052 mol) in 50 mL hexanes. White precipitation appeared after the addition started and the reaction was exothermic. The reaction mixture comprising LiNEt₂ was allowed to warm to room temperature. Next, the LiNEt₂ mixture was added dropwise to 4.51 g [(MeN)₃TaCl₂]₂ (5.87 mmol) in 100 mL hexanes at room temperature and stirred overnight. Following filtration, the dark brown filtrate was recovered. The volatiles from the filtrate were removed in vacuo at room temperature to yield 4.10 g of dark yellow (NEt₂)₂Ta(NMe₂)₃ (76% yield). Atomic percentage calculated for TaC₁₄H₃₈N₅: C, 36.76%; H, 8.37%; N, 15.31%. Found: C, 36.56%; H, 8.30%; N, 14.97%.

Figure 7:
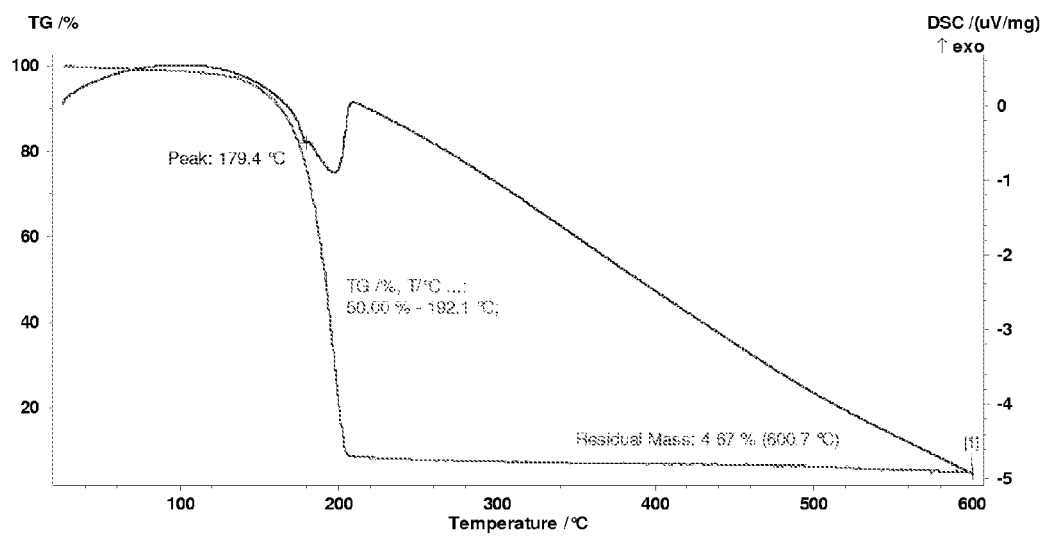
FIG. 7 is an STA plot of 6.28 mg (NEt$_2$)$_2$Ta(NMe$_2$)$_3$ in Ar.

FIG. 7 shows that (NEt₂)₂Ta(NMe₂)₃ is stable to heat up to its boiling temperature and undergoes complete material transport below 200° C.

Figure 8:
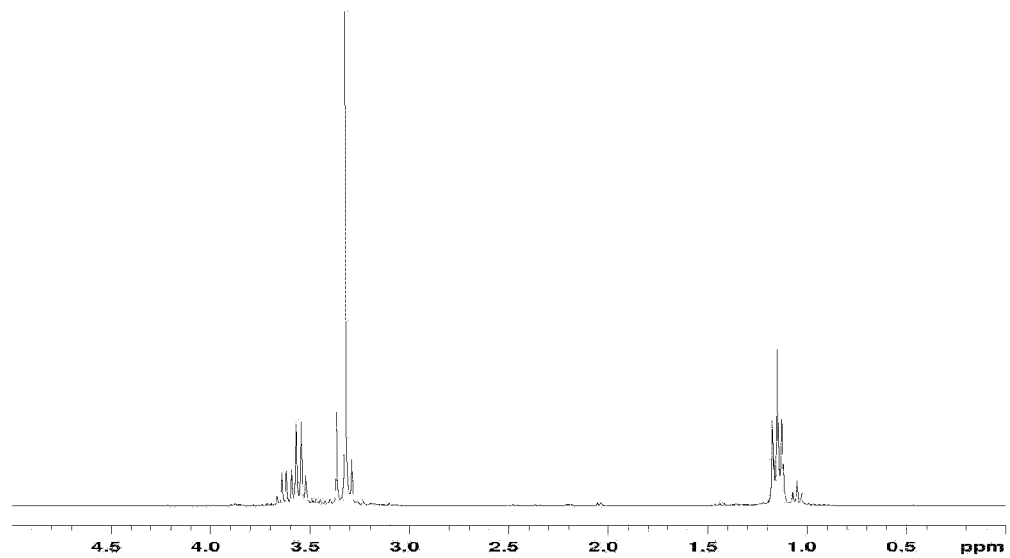
FIG. 8 is a $^1$H NMR plot for (NEt$_2$)$_2$Ta(NMe$_2$)$_3$ in toluene-d$_8$.

FIG. 8 shows the ¹H NMR plot of (NEt₂)₂Ta(NMe₂)₃ in toluene-d₈ at 21° C. ¹H NMR: δ 3.56 (m, 8H, CH₃CH₂N—); 3.29 (m, 18H, (CH₃)₂N—); 1.14 (m, 12H, CH₃CH₂N—). ¹³C NMR: δ 47.64, 46.69 (CH₃CH₂N—); 47.31, 47.09 ((CH₃)₂N—); 16.7, 16.0 (CH₃CH₂N—). The NMR spectra are consistent with the assigned structure; the complicated patterns in the ¹H spectra were attributable to cis- and trans- isomers in the solution:

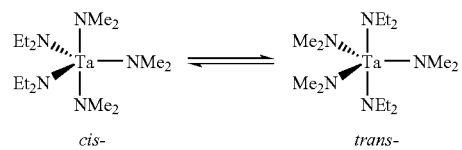

cis-    trans-

While the invention has been described illustratively herein with respect to specific aspects, features and embodiments thereof, it is to be appreciated that the utility of the invention is not thus limited, but rather extends to and encompasses other aspects, features and embodiments, such as will readily suggest themselves to those of ordinary skill in the art, based on the disclosure herein. The invention therefore is intended to be broadly construed and interpreted, as including all such aspects, features and alternative embodiments within the spirit and scope of the claims set forth hereafter.

What is claimed is:

1. A precursor vapor for depositing tantalum in a vapor deposition process, said precursor vapor comprising η²-N, N'-dimethylethylenediamino-tris-dimethylaminotantalum, (η²-MeN(CH₂)₂NMe)Ta(NMe₂)₃ (DEMAT), vapor.

2. A liquid precursor for depositing tantalum in a vapor deposition process, said liquid precursor being constituted by neat liquid η²-N,N'-dimethylethylenediamino-tris-dimethylaminotantalum, η²-MeN(CH₂)₂NMe)Ta(NMe₂)₃ (DEMAT).

3. The liquid precursor of claim 2, wherein said neat liquid DEMAT comprises high purity DEMAT.

4. A method of forming a tantalum-containing barrier layer on a substrate, comprising vapor deposition of tantalum on said substrate from vapor of a precursor comprising η²-N,N'-dimethylethylenediamino-tris-dimethylaminotantalum, η²- MeN(CH₂)₂NMe)Ta(NMe₂)₃ (DEMAT).

5. The method of claim 4, wherein the tantalum-containing barrier layer comprises a barrier layer selected from the group consisting of TaN, Ta₂O₅, TaSiN and BiTaO₄ barrier layers.

6. The method of claim 4, wherein the tantalum-containing barrier layer comprises a TaN barrier layer.

7. The method of claim 4, wherein the tantalum-containing barrier layer comprises a Ta₂O₅ barrier layer.

8. The method of claim 4, wherein the tantalum-containing barrier layer comprises a TaSiN barrier layer.

9. The method of claim 4, wherein the tantalum-containing barrier layer comprises a BiTaO4 barrier layer.

10. The method of claim 4, wherein said vapor deposition comprises Atomic Layer Deposition or Chemical Vapor Deposition.

11. The method of claim 4, wherein said vapor deposition comprises liquid delivery vapor deposition.

12. The method of claim 4, wherein said substrate comprises a microelectronic device structure.

13. The method of claim 12, wherein said microelectronic device structure comprises integrated circuitry.

14. The method of claim 13, wherein said integrated circuitry includes copper metallization and/or ferroelectric layers.

15. The method of claim 13, wherein said integrated circuitry includes copper metallization.

16. The method of claim 13, wherein said integrated circuitry comprises at least one ferroelectric layer.

17. The method of claim 4, wherein said vapor deposition comprises Atomic Layer.

18. The method of claim 4, wherein said vapor deposition comprises Chemical Vapor Deposition.

19. A method of making $\eta^2$-N,N'-dimethylethylenediamino-tris-dimethylaminotantalum (DEMAT), comprising:
reacting n-butyl lithium with N,N'-dimethylethylenediamine, to yield $(CH_3)NLi(CH_2)_2LiN(CH_3)$; and
reacting $(CH_3)NLi(CH_2)_2LiN(CH_3)$ with $[(MeN)_3TaCl_2]$ to yield DEMAT.

20. A method of manufacturing integrated circuitry including copper metallization and/or ferroelectric layers, and a tantalum-based barrier layer, said method comprising forming said barrier layer by deposition of tantalum from a precursor comprising $\eta^2$-N,N'-dimethylethylenediamino-tris-dimethylaminotantalum (DEMAT).

* * * * *